US011359300B1

(12) United States Patent
Beer et al.

(10) Patent No.: US 11,359,300 B1
(45) Date of Patent: Jun. 14, 2022

(54) ELECTROCHEMICAL METHOD FOR ENZYME IMMOBILIZATION ON BIOSENSOR ELECTRODES

(71) Applicant: LAXMI THERAPEUTIC DEVICES, INC., Goleta, CA (US)

(72) Inventors: Leanne Beer, San Francisco, CA (US); Isabella Camille Darke, Boston, MA (US); Ashley Nicole Farnkopf, Santa Barbara, CA (US); William Peter Van Antwerp, Santa Clarita, CA (US)

(73) Assignee: Laxmi Therapeutic Devices, Inc., Goleta, CA (US)

( * ) Notice: Subject to any disclaimer, the term of this patent is extended or adjusted under 35 U.S.C. 154(b) by 0 days.

(21) Appl. No.: 17/187,076

(22) Filed: Feb. 26, 2021

(51) Int. Cl.
*G01N 27/327* (2006.01)
*C25D 9/02* (2006.01)
*C12Q 1/00* (2006.01)
*A61B 5/1486* (2006.01)
*A61B 5/145* (2006.01)

(52) U.S. Cl.
CPC ............ *C25D 9/02* (2013.01); *A61B 5/14532* (2013.01); *A61B 5/14865* (2013.01); *C12Q 1/006* (2013.01); *G01N 27/3271* (2013.01); *A61B 2560/0214* (2013.01); *A61B 2562/12* (2013.01)

(58) Field of Classification Search
CPC ......................................... G01N 27/327–3278
USPC ..... 204/403.01–403.15; 205/777.5–778, 792
See application file for complete search history.

(56) References Cited

U.S. PATENT DOCUMENTS

| 5,166,063 | A | * | 11/1992 | Johnson | ................ | C12Q 1/003 |
| | | | | | | 435/173.2 |
| 6,814,845 | B2 | * | 11/2004 | Wilson | ................... | C12Q 1/001 |
| | | | | | | 204/486 |
| 2009/0143658 | A1 | * | 6/2009 | Petisce | ................... | A61B 5/415 |
| | | | | | | 600/345 |
| 2009/0294277 | A1 | * | 12/2009 | Thomas | ............ | G01N 27/3272 |
| | | | | | | 204/192.1 |
| 2012/0283538 | A1 | * | 11/2012 | Rose | .................. | G01N 27/3272 |
| | | | | | | 600/347 |

(Continued)

FOREIGN PATENT DOCUMENTS

| CN | 1782701 | * | 6/2006 |
| CN | 111239213 | * | 12/2020 |
| RU | 2633086 | * | 10/2017 |

OTHER PUBLICATIONS

Geise et al., Electropolymerized Films to Prevent Interferences and Electrode Fouling in Biosensors, Biosensors & Bioelectronics, 6, 1991, 151-160 (Year: 1991).*

(Continued)

*Primary Examiner* — Bach T Dinh
(74) *Attorney, Agent, or Firm* — Lewis Roca Rothgerber Christie LLP

(57) ABSTRACT

A method for forming an enzymatic biosensor includes preparing a first deposition solution comprising an enzyme, placing a substrate in the first deposition solution, applying an electrical potential to a working electrode of the substrate to deposit the enzyme on the working electrode, placing the substrate in a second deposition solution comprising electropolymerizable monomers, and passing a current through the working electrode to polymerize the monomers to form an electropolymerized polymer layer over the enzyme deposited on the working electrode.

20 Claims, 16 Drawing Sheets

(56) References Cited

U.S. PATENT DOCUMENTS

2017/0128009 A1* 5/2017 Pushpala .......... A61B 5/150969
2020/0405200 A1* 12/2020 Du .................... A61B 5/14532

OTHER PUBLICATIONS

CN 1782701 English translation (Year: 2006).*
CN111239213 English translation (Year: 2020).*
RU2633086 English translation (Year: 2017).*

* cited by examiner

ELECTROCHEMICAL METHOD FOR ENZYME IMMOBILIZATION ON BIOSENSOR ELECTRODES

BACKGROUND

Field

The present disclosure generally concerns medical devices and tools used for measuring analytes in the body. More specifically, embodiments of the invention relate to a method for immobilizing and stabilizing an enzyme matrix on an electrode of a medical device used for measuring analytes in the body, such as at a working electrode of an electrochemical biosensor.

Description of Related Art

Recent years have seen increased interest in wearable sensors for measuring analytes in the body (e.g., glucose levels), because such sensors might greatly ease analyte measurement. In particular, there has been growing interest for wearable sensors that selectively measure analytes that must be continuously monitored or at least frequently monitored. For example, monitoring glucose levels is particularly important for individuals suffering from type 1 or type 2 diabetes. People with type 1 diabetes are unable to produce insulin or produce very little insulin, while people with type 2 diabetes are resistant to the effects of insulin. Insulin is a hormone produced by the pancreas that helps regulate the flow of blood glucose from the bloodstream into the cells in the body where it can be used as a fuel. Without insulin, blood glucose can build up in the blood and lead to various symptoms and complications, including fatigue, frequent infections, cardiovascular disease, nerve damage, kidney damage, eye damage, and other issues. Individuals with type 1 or type 2 diabetes need to monitor their glucose levels in order to avoid these symptoms and complications. Other analytes that can use this same type of enzyme-based technology include lactate (athletes, sepsis), cholesterol, creatinine (CKD), hydroxybutyrate (ketones), urease (kidney diseases), bilirubin, and many others.

Traditionally, glucose has been monitored in capillary blood, typically from a fingertip. A user of these traditional glucose measuring devices would prick a fingertip with a blood lancet to produce a drop of blood. The user would place the drop of blood on a test strip after inserting the test strip into the meter; the meter would then measure the glucose concentration in the blood. Although widely used, traditional glucose monitoring devices are limited because they can only measure blood glucose levels at a single point in time. This can be problematic because blood glucose levels can fluctuate throughout a day, especially after food is digested. Regular monitoring of blood glucose levels may require multiple finger prick measurements, which may be prone to some technique errors and/or other variations based on inconsistent user and external variables. In addition, frequent blood pricks can be painful or otherwise overly intrusive, and users may be hesitant to take a sufficiently appropriate number of blood glucose measurements to get any sort of glucose rate of change data. Rate of change data is particularly important for patients dosing insulin since a proper meal bolus needs to be adjusted for the current glucose rate of change. For example, if a patient eats a 100 g carbohydrate meal that would need 6 units of insulin based on her insulin sensitivity, the correct dose would be 5.7 U if the BG is going down at more than 1.5 mg/dl-min and would be 6.2 or 6.3 U if the BG is rising. Only CGM systems can give the patient that type of information.

SUMMARY

In contrast to traditional glucose monitors, wearable devices can allow for continuous glucose monitoring (e.g., continuous glucose monitors (CGM)). CGMs are always active and continuously measure glucose levels at set intervals (e.g., measured every ten seconds and readings reported every five minutes). The continuous data can allow users to track glucose levels over the course of a day or over a few days and help users make more informed decisions about their diet, physical activity, and medications. CGMs operate by inserting a small sensor under the skin, typically on the abdomen or the back of the upper arm, although sensors have been worn on other parts of the body including the thighs, lower back, and buttocks. FIGS. 1A and 1B show examples of wearable devices that are worn on a human body, where in FIG. 1A a CGM 1 is worn or otherwise attached to the abdomen or torso region of a patient or subject, and in FIG. 1B the CGM 1 is alternatively worn or otherwise attached to an upper arm of a patient or subject. Other sensors may also be worn on other parts of the body. The sensors can be held in place by an adhesive and can wirelessly transmit glucose measurements to, for example, a separate monitoring device. However, unlike finger stick capillary blood devices, CGMs instead measure glucose in interstitial fluid (e.g., glucose in the fluid between cells) rather than glucose in blood directly.

An example of a wearable CGM is schematically shown in FIGS. 2A to 3. FIG. 2A shows a perspective view of an embodiment of a wearable CGM 1, FIG. 2B shows a side view of the wearable CGM 1, and FIG. 2C shows a bottom view of the wearable CGM 1. The CGM 1 may generally include a body or housing 10 having a top end 11 and a bottom end 12. An adhesive 13 may be found on the bottom end, and may be in the form of, for example, a tape that has a perimeter that extends slightly outside of the perimeter of the housing 10, to improve adhesion to the patient's body. At the bottom end 12, there may also be a hole or opening 14, through which a needle sensor 15 extends. The needle sensor 15 may only protrude slightly out of the bottom end 12 and may be connected in the housing to another circuitry. FIG. 3 shows a schematic block diagram of the CGM 1. The needle sensor 15 may be connected to a PCB 16 or another circuitry. The PCB 16 may further include or be otherwise connected to a transmitter/receiver 17, a controller 18, and a battery 19. The transmitter/receiver 17 allows the CGM 1 to communicate with a separate monitoring device, the controller 18 can control functionality and monitoring of the CGM 1, and the battery 19 can supply power to the components of the CGM 1.

The above analyte measurement methods, including monitoring with CGMs, are still categorized as invasive, that is, they require entry into the body or a body cavity (e.g., where a probe is used to percutaneously access the body fluid being analyzed). In contrast, non-invasive glucose monitoring methods have also been explored but have proven difficult to implement for various reasons such as reduced accuracy. Meanwhile, invasive methods have traditionally used a probe in the form of a thin flexible sensor inserted into the lipid layer of the skin approximately 6-9 mm below the surface. Historically, there has been more limited interest in rigid needle-based wearable analyte sensors because of recognized difficulties in designing and manufacturing a sufficiently compact and reliable needle-based system. To address this and similar issues, needles can, for example, be integrated with electrodes that can be used for various applications, including electrochemical sensing and electrical stimulation.

In addition, for example as seen in embodiments of the invention, needles can also be integrated with enzyme matrices. An enzyme is a catalyst that can speed up the rate of a chemical reaction without itself being altered in the chemical reaction. The composition of the enzyme matrix can depend on the analyte being measured. For example, CGMs may have sensors that incorporate glucose oxidase (GOx) enzyme matrices. GOx is an enzyme that catalyzes the oxidation of glucose into hydrogen peroxide ($H_2O_2$) and gluconolactone ($C_6H_{10}O_6$). The chemical formula for the oxidation of glucose is provided below:

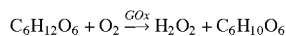

$$C_6H_{12}O_6 + O_2 \xrightarrow{GOx} H_2O_2 + C_6H_{10}O_6$$

Using this formula, CGMs calculate blood glucose levels by measuring the amount of hydrogen peroxide produced by the oxidation of glucose. To this end, the CGM sensors can, for example, have a working electrode that uses a fixed potential electrochemical measurement technique where the hydrogen peroxide is oxidized (e.g., undergoes an oxidation reaction) and the electrical current produced is measured as the sensor signal. Based on measurement of the electrical current, the CGM can determine the concentration of glucose.

An example of a needle sensor for a CGM is schematically shown in FIGS. 4A-4C. FIG. 4A shows a perspective view of a needle sensor 15, FIG. 4B shows a top view of the needle sensor 15, and FIG. 4C shows a close-up view of a tip of the needle sensor 15 including the sensor portion. The needle sensor 15 includes a base 151, a shaft 152, and the needle tip 153. The needle tip 153 may include various electrodes 154a, 154b, and 154c that facilitate the glucose monitoring. The electrodes 154a, 154b, 154c are electrically connected to corresponding larger contacts 155a, 155b, 155c at the base, for easy connectivity with the PCB 16 of FIG. 3.

In CGMs, enzyme systems may be functionalized on a sensor by a number of methods, including submerging the sensor into a deposition solution during manufacturing or drop coating the enzyme matrix onto the sensor surface. The deposition solution may include a mixture of components, including a particular concentration of the desired enzyme and a protein. In both of these cases, the enzyme in the deposition solution can form a layer on the needle surface via intermolecular interactions. However, the enzyme layer may form over undesired parts of the sensor producing hydrogen peroxide which does not contribute to the signal. This non-specific hydrogen peroxide may diffuse into the tissue in vivo leading to potential tissue irritation.

Additionally, CGM sensors that use GOx and measure hydrogen peroxide will have an oxygen deficit problem. In the glucose oxidation reaction, one mole (M) of oxygen is needed for one mole of glucose. In the body tissue, oxygen levels are typically 20 µM while tissue glucose concentration can be as high as 28 mM (500 mg/dl).

Moreover, problems particularly arise with cost-effective manufacturing of small and structurally robust needles with integrated electrodes. Very small needles (e.g., microneedles) are desired to reduce sensor size and minimize user sensation (e.g. pain or discomfort) during needle insertion, but traditional methods of manufacturing microneedles produce needles of silicon (via conventional silicon micromachining or use of structural lithography resists, e.g., SU-8 photoresists), or plastic needles (via micro molding methods). Silicon microneedle arrays are limited in length by the thickness of available silicon wafers (a wafer is no more than 750 microns thick) and thus are limited to 400 or so microns in length which are not long enough to reach the true dermis. Molded plastic microneedle arrays are not mechanically strong enough at lengths that are in the 1-1.5-millimeter range.

The exemplary embodiments of the present invention disclosed herein are directed to an electrochemical method for enzyme immobilization on biosensor electrodes.

Embodiments of the present disclosure include a method for immobilizing and stabilizing an enzyme matrix on a working electrode of an electrochemical biosensor. In some embodiments, the working electrode of the electrochemical biosensor can be used to measure analytes in the body (e.g., glucose levels).

According to various embodiments of the present disclosure, the method incorporates complementary electrochemical techniques that can deposit an inner enzymatic sensing layer and an outer polymer membrane in a highly selective and easily controllable manner. The techniques for depositing an enzyme matrix include constant voltage, constant current DC, AC with unbalanced positive and negative voltages as well as a sequence of pulses of various durations and voltages. In general, enzymes and other proteins have an isoelectric point (pI) in the pH 4-5 range. Glucose oxidase has a pI of 4.2. This means that at pH 7, the enzyme is predominantly negatively charged. At pH 3.5 the enzyme is predominantly positively charged. For electro-osmotic delivery, both low and high pH matrices can be used. At pH 7.4 a positive charge on the working electrode will pull enzyme to the electrode, while at pH 3.5 a negative charge will do the same. In some preferred embodiments, the complementary electrochemical techniques can include galvanostatic adsorption of an enzyme matrix and electropolymerization of membrane via cyclic voltammetry.

The galvanostatic adsorption technique involves holding a constant current at an electrode while the electrode is immersed in an electrolyte which contains the species to be absorbed on the electrode (e.g., a deposition solution). The polarization of the electrode can be controlled by maintaining the electrode at a constant current. Based on the polarization of the electrode, certain compounds can be attracted (e.g., drawn by electrostatic forces) to the surface of the electrode. In some embodiments, the polarization of the electrode can be adjusted to attract enzymes in the deposition solution to the electrode surface. The electrostatic forces can hold the enzyme at the surface of the electrode. It is well understood that other approaches can also be used as described in herein, such as unbalanced AC deposition, constant voltage deposition and pulse sequence deposition.

The electrochemical polymerization technique is a process for creating polymer films on an electrode by controlling the number of electric potential cycles or current that is applied to the electrode while immersed in an electrolyte containing monomeric species (e.g., a monomer that can be polymerized by applying an appropriate voltage/current). Such monomers are electro-polymerizable). As with the deposition of the enzyme, several electrochemical approaches can be used to create the electropolymerized polymers. These may include constant voltage, constant current, cyclic voltammetry, unbalanced AC as well as a series of pulses with constant or varying voltages and times. Electrodeposited polymers can be either conducting or non-conducting, and the polymer system is chosen for specific analytical reasons. Some examples of conducting polymers are pyrrole, thiophene, Indole, carbazole, Triphenylene and many of their derivatives. Some non-conducting electropolymers are those made from Phenol and phenol derivatives, phenylene diamines, chlorophenyl amide, and tyramine. Tyramine is one of the most interesting since it has a free amino group that can be used to covalently crosslink the enzyme to the actual monomer.

In some embodiments, cyclic voltammetry (CV) can be used to create the polymer layer on the electrode. In cyclic voltammetry, the potential of the working electrode is scanned over a specific range and cycled such that the resulting current can be measured. For example, a potential scan can begin from a greater potential and end at a lower potential. The scan can then cycle from the lower potential back to the greater potential. The current created by the cycle changes can create a polymer film on the surface of the working electrode due to oxidation or reduction of the monomeric species in the deposition solution for this process.

Enzymes after deposition need to be immobilized to preserve their enzymatic activity. Immobilization is typically done by crosslinking the enzyme either to itself, to another protein such as albumin, or by covalent attachment to the electropolymerized polymer overlayer. There are multiple methods for crosslinking of the enzyme including glutaraldehyde and other di-aldehydes, carbo-diimides of varying chain lengths and a wide variety of heterobifunctional reagents with two different bonding domains.

The enzyme immobilization method can be used in various enzymatic sensing systems, including, but not limited to, sensing systems that measure lactate, alcohol, or glucose. In some embodiments, the method can be used for immobilizing and stabilizing an enzyme matrix on a glucose sensor. Glucose oxidase (GOx) is one possible enzymatic species that can be used with the glucose sensor but other enzymatic species, such as glucose dehydrogenase, may also be incorporated.

According to one embodiment, GOx can be adsorbed on the surface of the glucose sensor using galvanostatic adsorption. In the galvanostatic adsorption step, a current can pass through the working electrode to create an electrical charge that attracts the negatively charged GOx dissolved in a solution with pH higher than the isoelectric point to the surface of the working electrode. Alternatively, the GOx can be driven to the electrode with a negative voltage if the GOx is dissolved in a solution where the pH is below the pI. The galvanostatic attraction increases the amount of enzyme coated on the sensor, while maintaining a controlled deposition at the working electrode only. In some embodiments, a crosslinking partner (e.g., another protein (e.g., stabilizing protein) that can be used as a crosslinking partner to increase enzyme stability) can be included. In some embodiments, Human serum albumin (HSA) can be used as a stabilizing protein for the GOx after crosslinking but other stabilizing proteins such as silk fibroin may be incorporated.

After the initial adsorption of GOx, cyclic voltammetry (CV) as well as fixed potential electropolymerization can be used to form a polymer membrane over the adsorbed GOx on the electrode surface. In some embodiments, the polymer layer can be a polytramine membrane however other polymeric systems can be used (e.g., polydopamine, m-phenylenediamine, o-phenylenediamine, polypyrrole). During the electropolymerization, a polymer film encapsulates the previously deposited enzyme, which provides stability and prevents the enzyme from diffusing away from the electrode surface. In some embodiments, the polymer layer can be glucose limiting (e.g., limit the amount of glucose that can pass through the polymer layer) and it can also limit the transport of interfering species into the sensor (e.g., ascorbic acid, acetaminophen).

The galvanostatic absorption and the cyclic voltammetry electropolymerization steps are relatively short (e.g., on the order of minutes/tens of minutes) and can be expanded to fabricate many devices in parallel. Also, the transition to using cyclic voltammetry instead of potentiostatic or galvanostatic techniques can result in higher yielding, more efficient, and repeatable depositions. This method also avoids the issues that arise with holding low currents and not reaching the necessary oxidation potentials.

Additionally, glutaraldehyde or other chemical induced crosslinking can also be applied to the glucose sensor to impart additional stability to the enzyme system. Glutaraldehyde can be utilized in the vapor or liquid state. In some embodiments, the crosslinking step could be added prior to CV electropolymerization or fixed potential electropolymerization of the polymer, to provide stability to the enzyme matrix by crosslinking the enzyme to stabilizers such as human serum albumin (HSA) prior to addition of polymer membrane. In other embodiments, the glutaraldehyde crosslinking step can be added after the addition of membrane. Using tyramine as an example, the pendant amine groups on the polymer backbone can crosslink directly to the enzyme matrix imparting additional stability to the system.

The electrochemical method for immobilizing the enzyme on the biosensor electrodes can be applied on various electrode types, including, different types of platinum (Pt) including, but not limited to, platinum wires, evaporated titanium platinum (TiPt), Pt black, and screen-printed Pt, as well as other electrode materials including carbon, iridium oxide, microtextured Pt, and a wide variety of nanoparticle based working electrodes.

The electrochemical method for immobilizing the enzyme on the biosensor electrodes disclosed herein provides various advantages. For example, the method is easily scalable and allows for controlled, repeatable deposition of enzymes within the confines of a working electrode. This method also conserves materials and prevents non-specific GOx adsorption onto other parts of the sensor, which mitigates any unnecessary hydrogen peroxide formation which could irritate the tissue in vivo. Additionally, the resulting polymer films can suppress potential interferents, such as acetaminophen or ascorbic acid, and have the potential to be naturally glucose-limiting.

DETAILED DESCRIPTION

Many previous wearable sensors required piercing of a patient's skin using a rigid needle combined with a separate typically soft or flexible, biosensor, where for example, the needle and biosensor pierce through the skin together (e.g., with the biosensor housed inside the needle), followed by removal of the needle to leave the biosensor in place under the skin. By forming a biosensor directly on a tip of a needle according to embodiments of the invention, the same needle can be used to pierce the skin, and can remain under the skin for sensing purposes, eliminating the requirement to manually remove the needle, and thereby reducing the steps needed by an end user to apply the wearable sensor, and potentially also reducing the likelihood of errors during application.

A needle sensor, e.g., where a sensor is integrated or otherwise formed directly on a rigid needle structure, can be accomplished in a variety of ways according to embodiments of the invention. Under one approach, a rigid needle substrate (e.g., a biosensor substrate formed as a needle) including, for example, a biocompatible metal, is first provided, and then a first insulating layer is applied on the substrate. In some embodiments, the insulating layer can then be metalized, or covered with a layer of metal. The sensor circuitry of the needle sensor can then be established using, for example, photolithographic techniques. Then, a second insulating layer may then be formed on the needle sensor to insulate the conductive traces of the circuitry formed on the needle, where for example, only the sensor electrodes and the electrical contacts remain exposed. Some nonlimiting examples of materials that can be used for the rigid substrate or other parts of such a needle sensor are stainless steel, titanium, and ceramics such as alumina or silica, or other non-metals. In addition, the various parts of the needle sensor can further be made of the same or of different materials. Other embodiments of forming a general structure of a general needle sensor that serves the dual purpose of skin puncturing and sensing may include more or less steps than those described above without departing from the scope of the invention. In other embodiments, the biosensors according to embodiments of the invention can also still be constructed on a more flexible substrate instead of on a more rigid substrate.

Figure 1A:
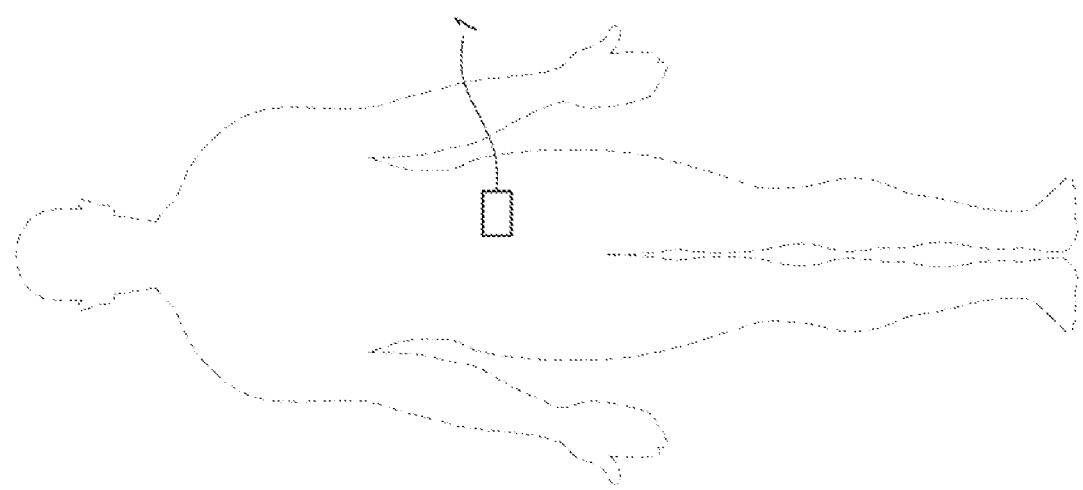
FIGS. 1A and 1B schematically show a wearable continuous glucose monitor (CGM) being worn on a patient's torso and on a patient's arm, respectively.
Figure 1B:
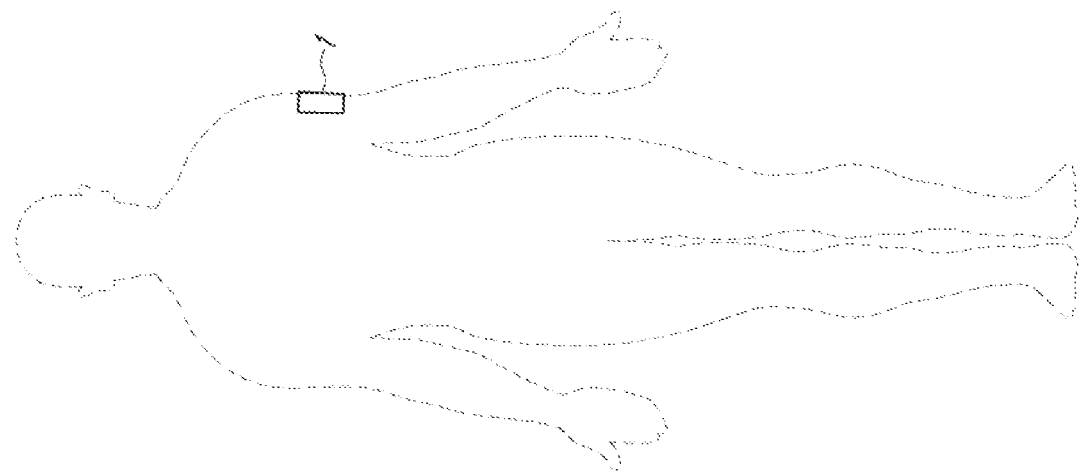
Figure 2A:
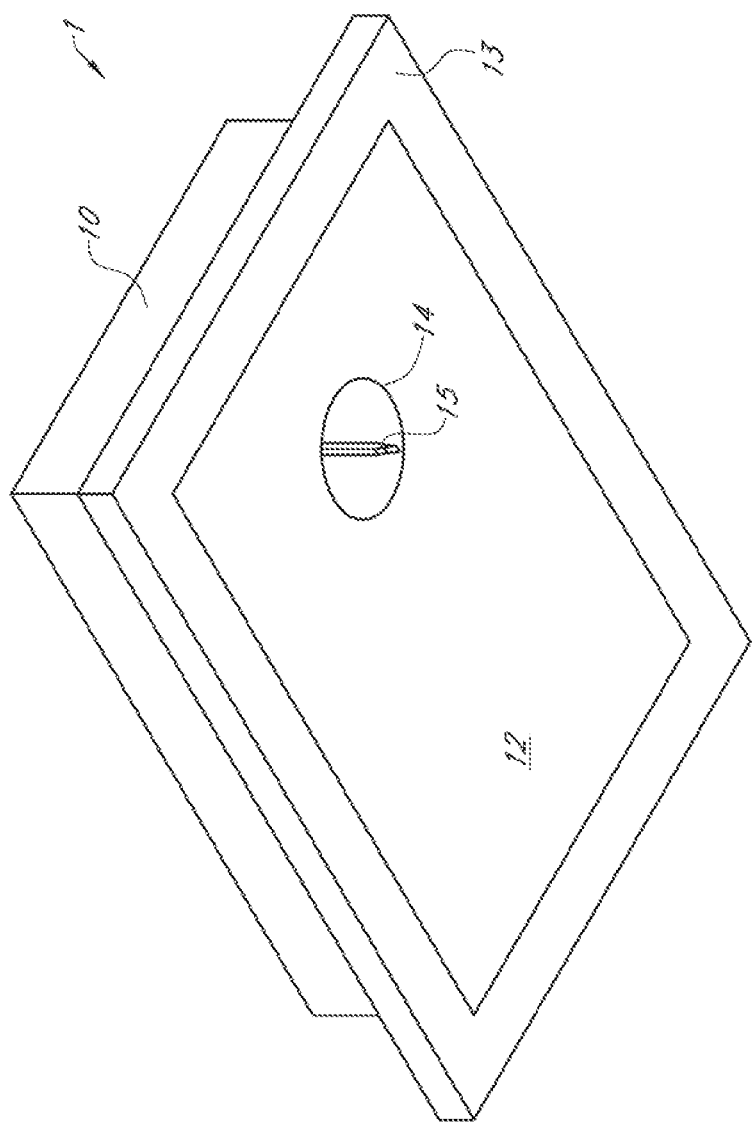
FIG. 2A-2C respectively show a perspective view, a side view, and a bottom view of an embodiment of a CGM according to an embodiment of the invention.
Figure 2B:
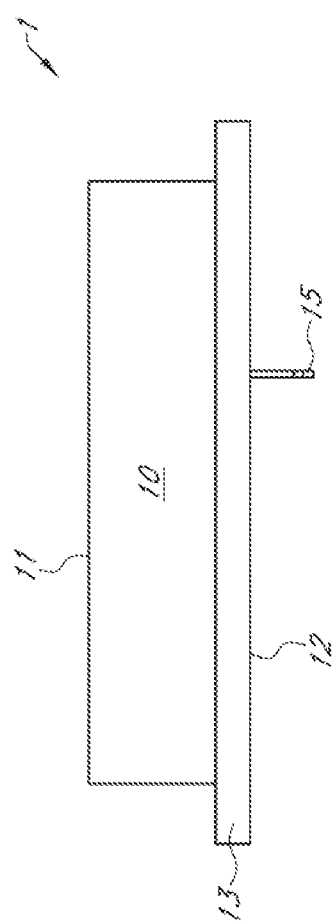
Figure 2C:
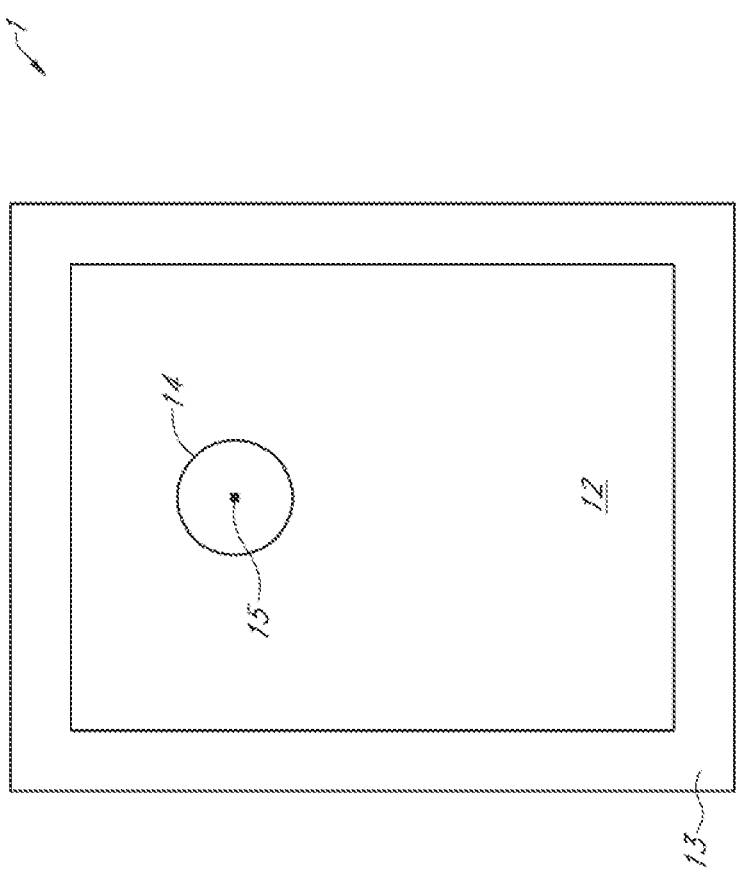
Figure 3:
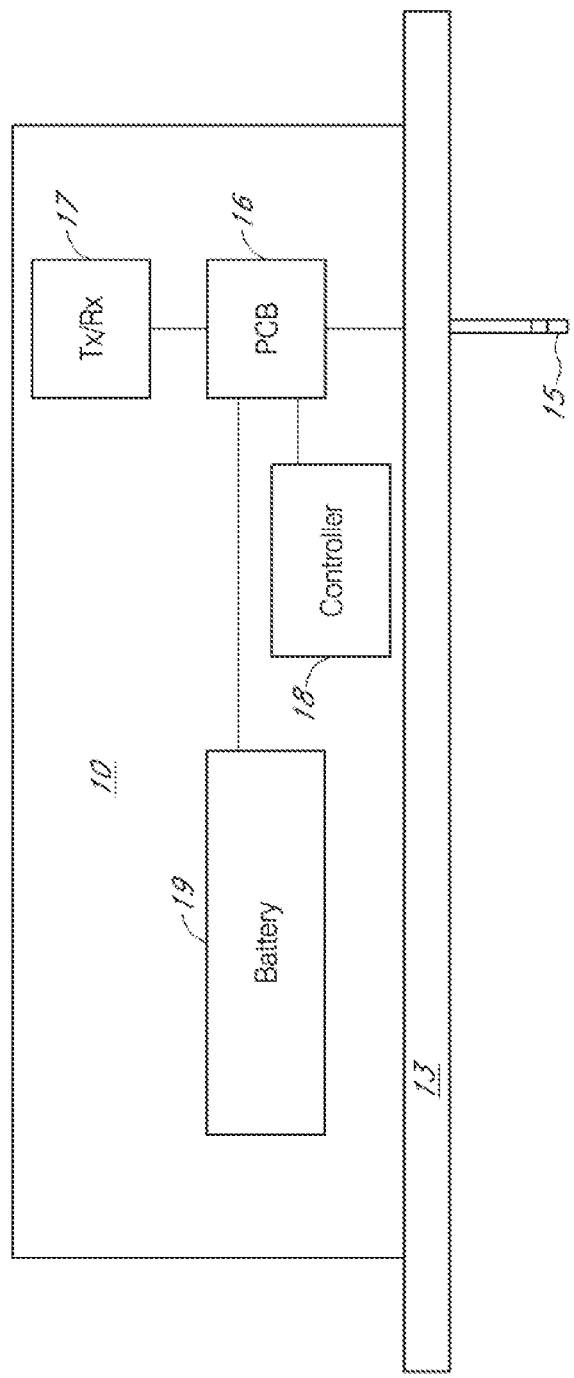
FIG. 3 shows a schematic block diagram of the CGM of FIG. 2.
Figure 4A:
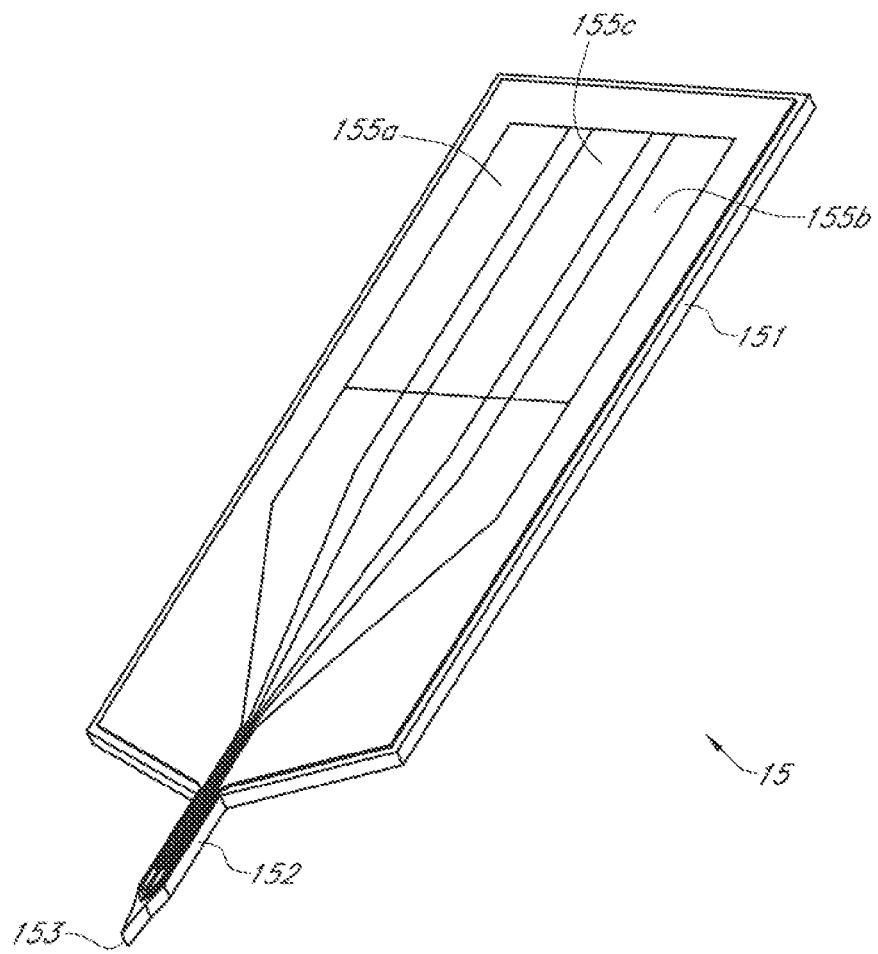
FIGS. 4A-4C respectively show a perspective view, a top view, and an enlarged view of a tip of a needle sensor of the CGM of FIGS. 2A-3.
Figure 4B:
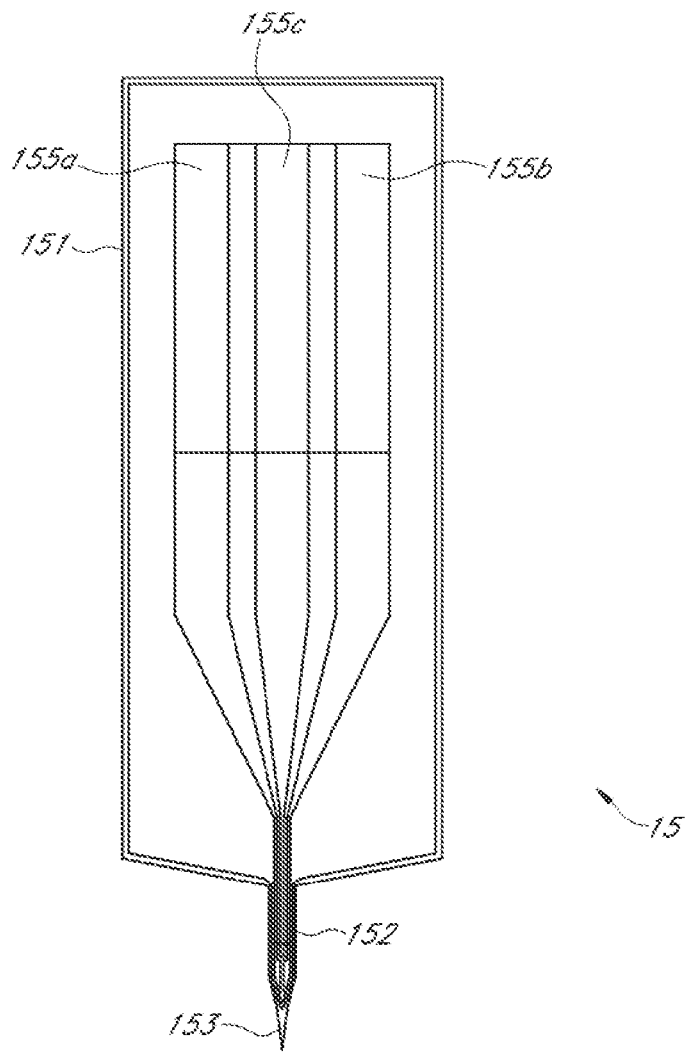
Figure 4C:
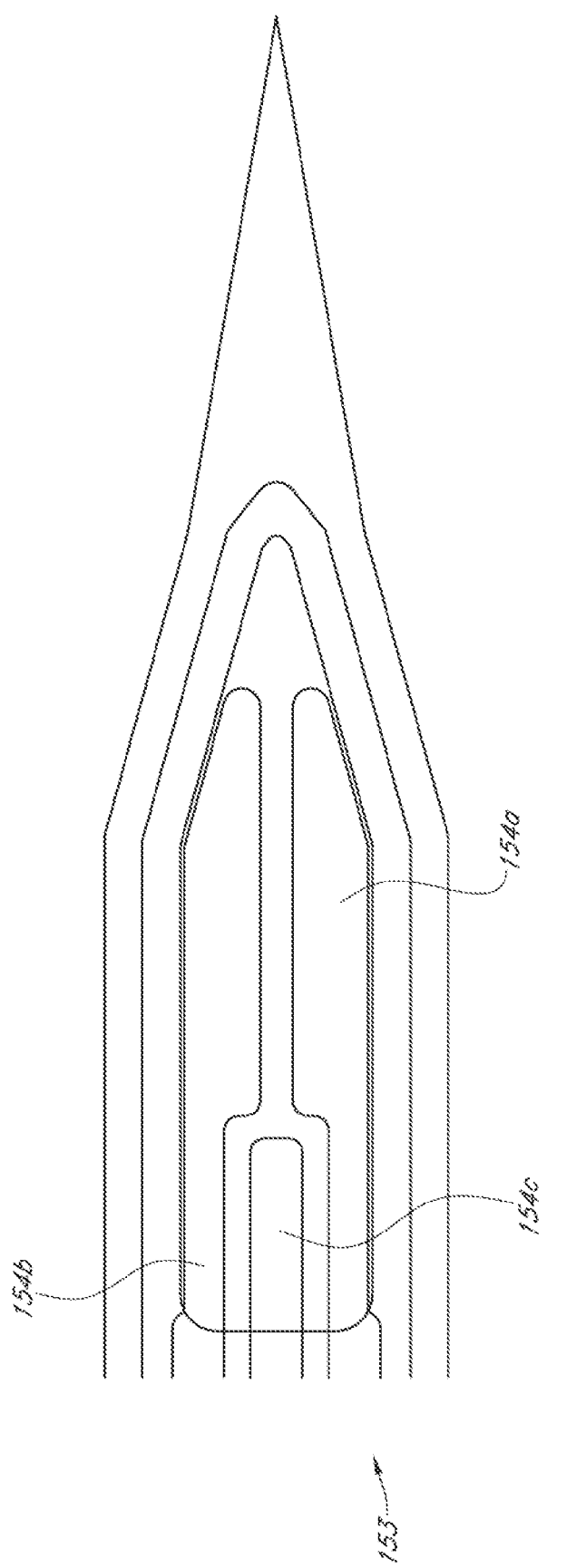
Figure 5:
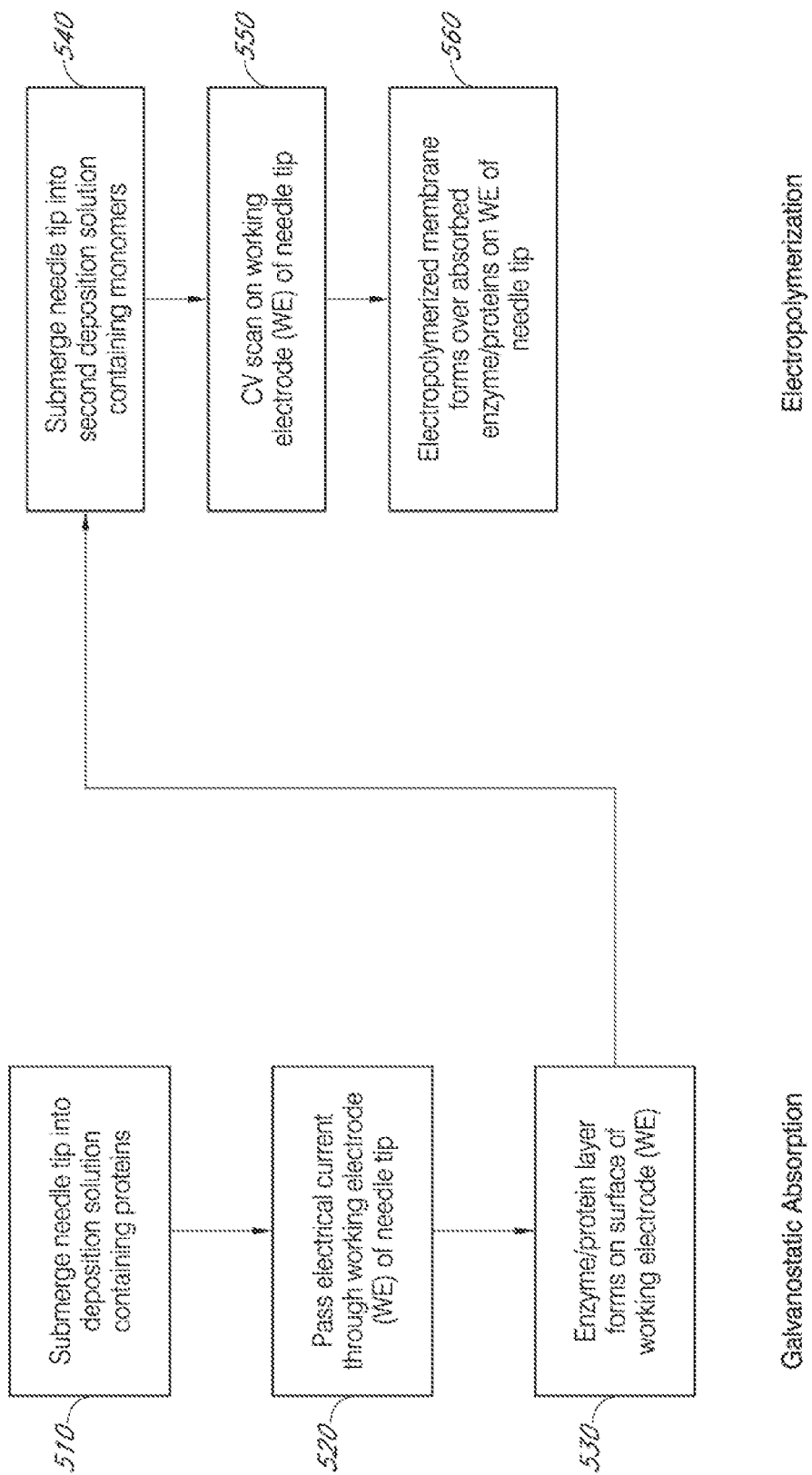
FIG. 5 is a flowchart showing a method for immobilizing an enzyme and diffusion limiting polymer on a working electrode of a biosensor needle tip, in accordance with example embodiments of the invention.

More detailed steps for forming a workable biosensor on a needle tip will now be described. FIG. 5 is a flowchart showing a method for immobilizing an enzyme and diffusion limiting polymer on a working electrode of a biosensor needle tip, in accordance with example embodiments of the invention. According to some example embodiments, the number and order of operations illustrated in FIG. 5 may vary. For example, according to some example embodiments, there may be fewer or additional operations, unless otherwise stated or implied to the contrary.

Referring to FIG. 5, the glucose oxidase (GOx) can be absorbed on the surface of the platinum black working electrode (WE) using galvanostatic adsorption. According to the galvanostatic adsorption technique, the needle sensor can be submerged into a deposition solution containing proteins in step 510. An external counter electrode (CE) and/or an external reference electrode (RE) can also be placed in the deposition solution. In some embodiments, the deposition solution can be composed of 4% wt/vol GOx in phosphate buffered saline (PBS). While the needle sensor is submerged in the deposition solution, an electrical current can be passed through the platinum black WE in step 520, for example, by utilizing the external CE and/or the external RE. In some embodiments, the current can be set at 1 µA and be held between 50 and 60 seconds. In other embodiments, the current may be held up to 120 seconds. The electric current polarizes the platinum black WE, which attracts the GOx in the deposition solution to the electrode surface. The electrostatic forces can hold the GOx and any stabilizing proteins at the surface of the WE in step 530.

Subsequently, a polymer membrane can be formed over the GOx and associated proteins on the surface of the WE using cyclic voltammetry or fixed potential (CV/FP) electropolymerization. This process involves removing the needle sensor from the initial deposition solution and submerging it into a different container having a second deposition solution containing monomers (e.g., electro-polymerizable monomers) in step 540. The external CE and/or the external RE can also be placed in the second deposition solution. In some embodiments, the second deposition solution can be composed of 5 mM tyramine in PBS. In step 550, CV can be used to reversibly scan the potential of the platinum black WE, for example, by utilizing the external CE and/or the external RE. In some embodiments, the range of the CV scan can be 0 to 1.4V at a scan rate of 10 mV/sec for 1 cycle. The CV scan can result in a polytramine membrane deposited over the absorbed GOx on the platinum black WE in step 560. The polytramine membrane may be glucose limiting.

Figure 6A:
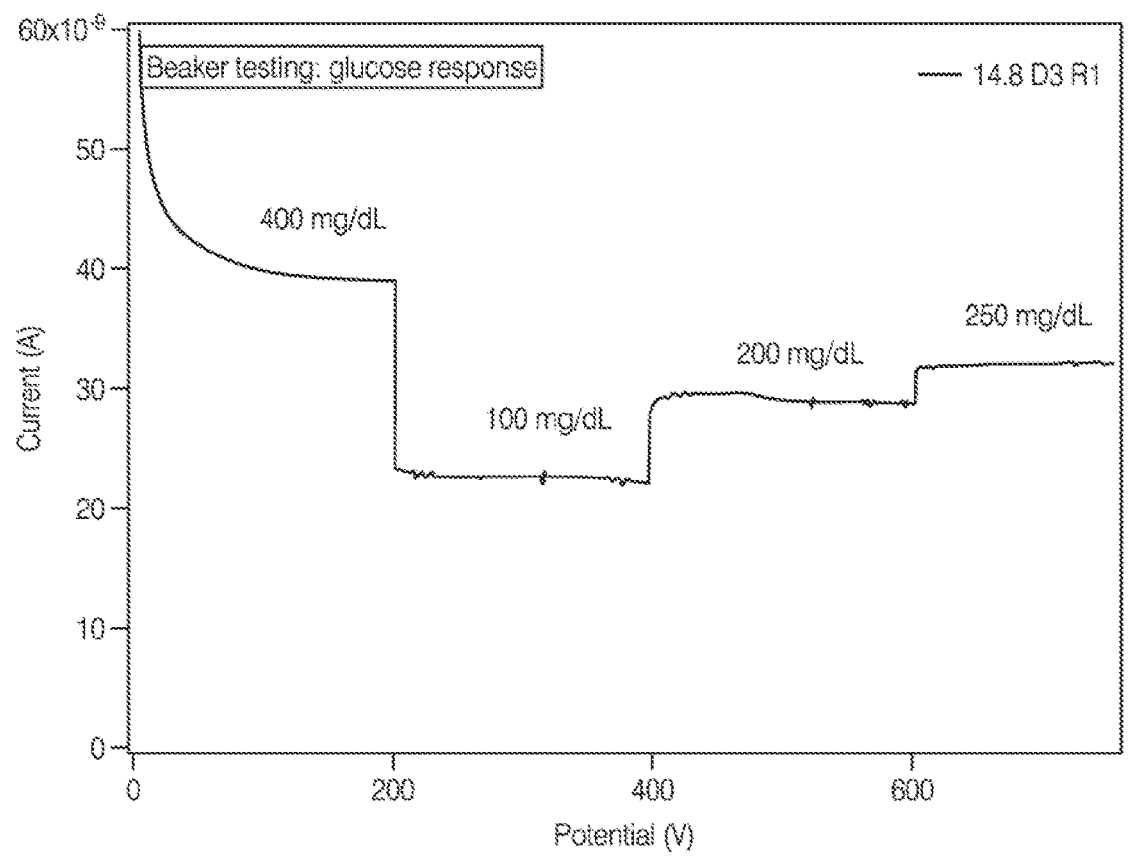
FIG. 6A shows the glucose response of a sensor that has been fabricated according to the method disclosed in FIG. 5 using a Pt black working electrode.

FIG. 6A shows the glucose response of a sensor that has been fabricated according to the method disclosed in FIG. 5.

Figure 6B:
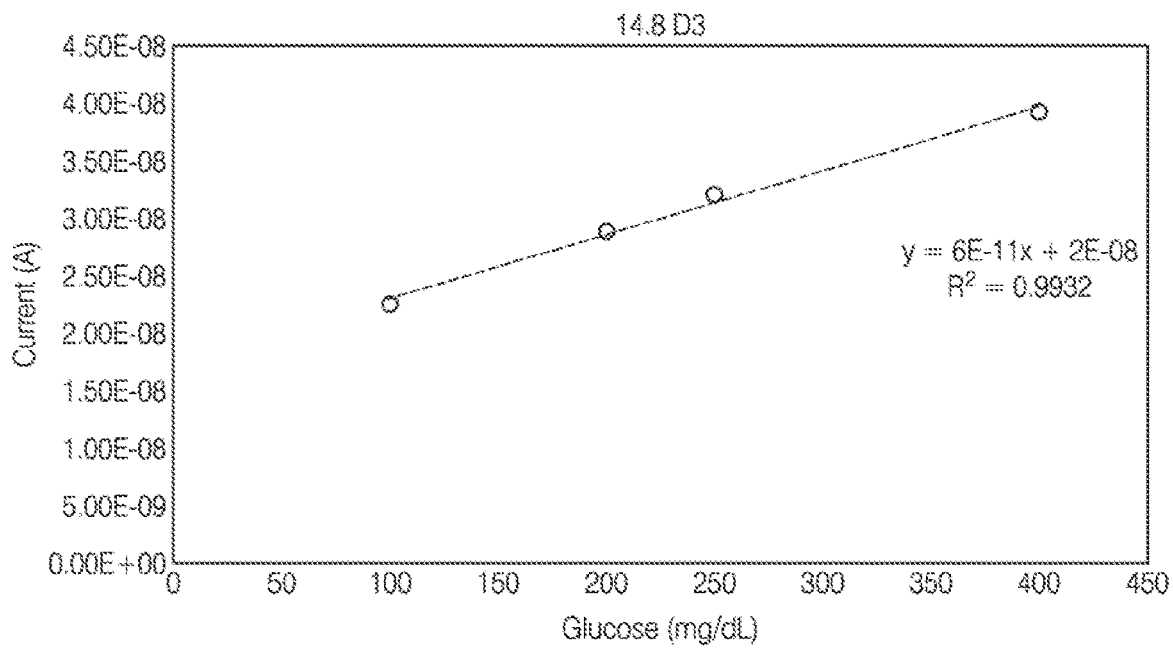
FIG. 6B shows the linear response of the sensor under the test conditions described in FIG. 5, where the working electrode is Pt black.

FIG. 6B shows the linear response of the sensor under these test conditions. In FIGS. 6A and 6B, the working electrode is Pt black.

In an alternative method similar to that shown in the method of FIG. 5, a stabilizing protein, such as human serum albumin (HSA), can be added to the deposition solution for the galvanostatic adsorption step on the platinum black WE. As with the method described above, according to some example embodiments, the number and order of operations may vary. For example, according to some example embodiments, there may be fewer or additional operations, unless otherwise stated or implied to the contrary.

In this alternative method, HSA can be incorporated into the deposition solution with GOx during the galvanostatic absorption step onto the platinum black WE according to some embodiments. The HSA stabilizes the GOx on the electrode surface after crosslinking, as the glutaraldehyde crosslinks the GOx proteins to the HSA and the HSA prevents GOx-GOx crosslinking which can destabilize the GOx. The GOx/HSA deposition solution can be composed of 4% wt/vol GOx and 4% wt/vol HSA in PBS. Similar to the method described previously, the needle sensor can be submerged in the GOx/HSA deposition solution with an external CE and/or an external RE. While the needle sensor is submerged in the deposition solution, an electrical current can be passed through the platinum black working electrode (WE) on the needle sensor, for example, by utilizing the external CE and/or the external RE. In some embodiments, the current can be set at 1 µA and be held between 50 and 60 seconds. In other embodiments, the current may be held up to 120 seconds. The electric current polarizes the platinum black WE, which attracts the GOx and HSA in the deposition solution to the WE surface. The electrostatic forces can hold the GOx and HSA at the surface of the platinum black WE.

Subsequently, a polymer membrane can be formed over the GOx on the surface of the platinum black WE using cyclic voltammetry (CV) electropolymerization. This process involves removing the needle sensor from the GOx/HSA deposition solution and submerging it into a different container having a second deposition solution containing monomers. The external CE and/or the external RE may also be placed in the second deposition solution. In some embodiments, the second deposition solution can be composed of 5 mM tyramine in PBS. Using, for example, the external CE and/or the external RE, a CV can be used to reversibly scan the potential of the platinum black WE, while the needle sensor is submerged in the second deposition solution. In some embodiments, the range of the CV scan can be 0 to 1.4V at a scan rate of 10 mV/sec for 1 cycle. The CV scan can result in a polytramine membrane deposited over the absorbed GOx and HSA on the platinum black WE surface. The polytramine membrane may be glucose limiting.

Figure 7A:
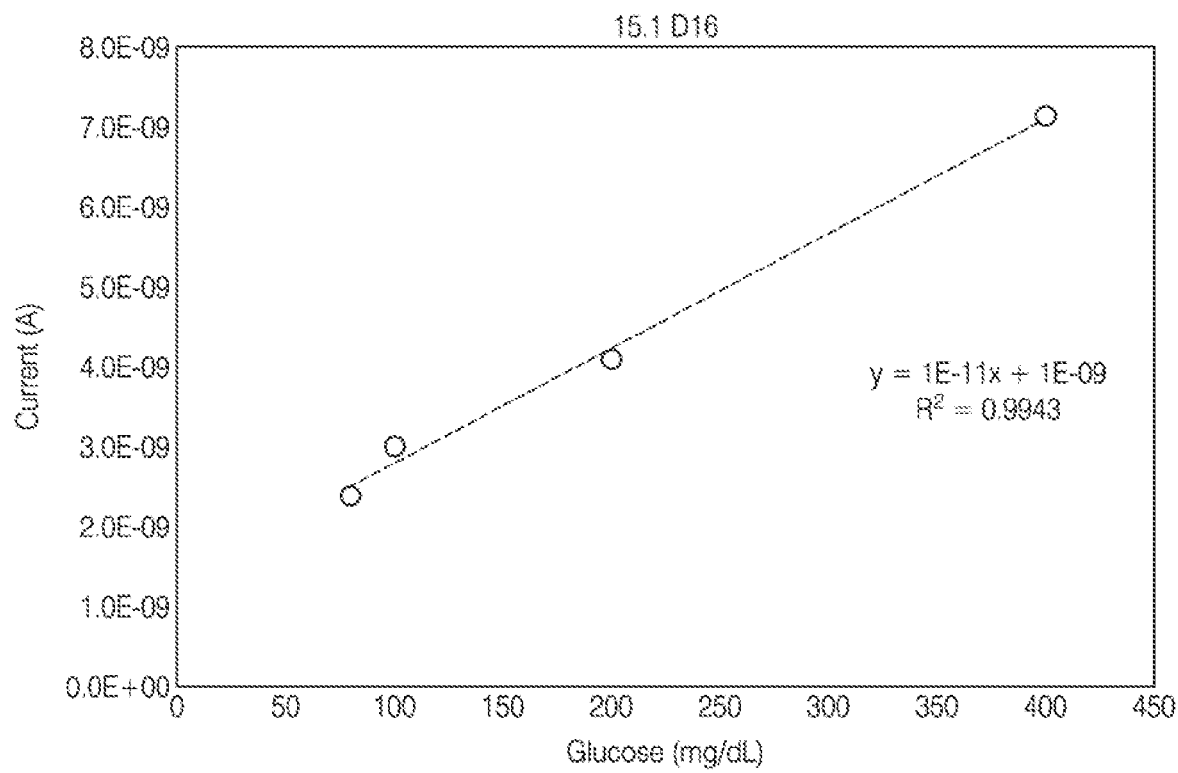
FIGS. 7A and 7B are additional examples of a linear response to glucose for sensors made according to a modified version of the method disclosed in FIG. 5, where the deposition solution also contains HSA stabilizer.
Figure 7B:
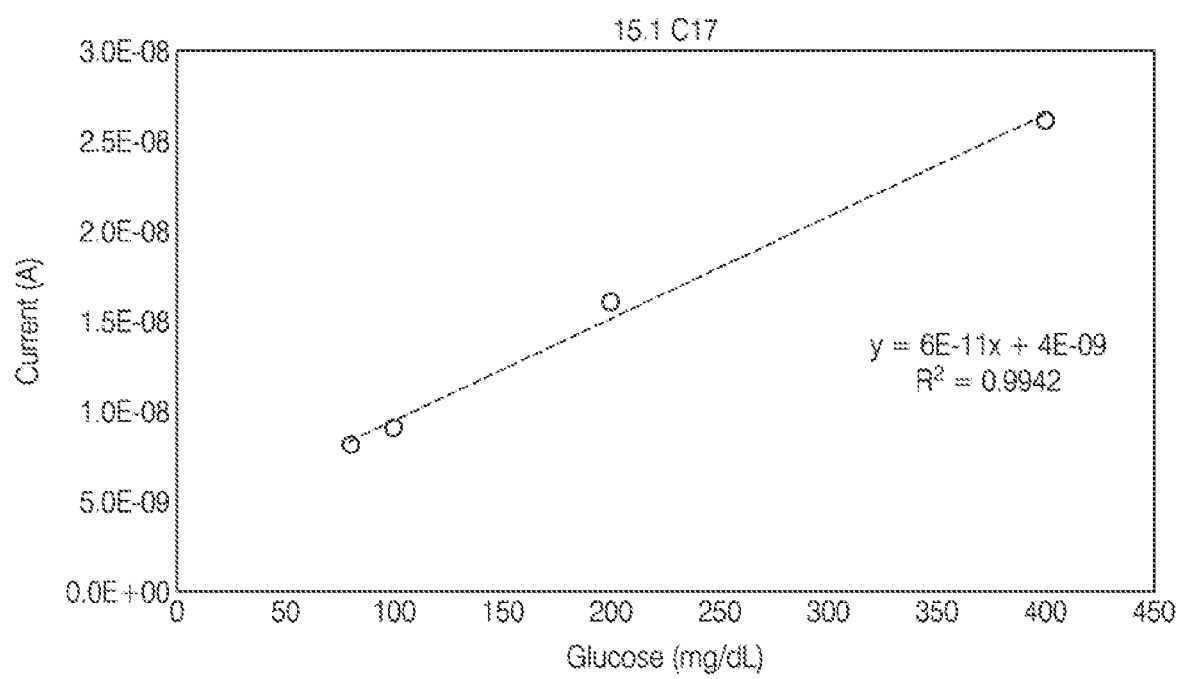

FIGS. 7A and 7B are additional examples of a linear response to glucose for sensors made according to a modified version of the method disclosed in FIG. 5 where the deposition solution also contains HSA stabilizer.

Figure 8:
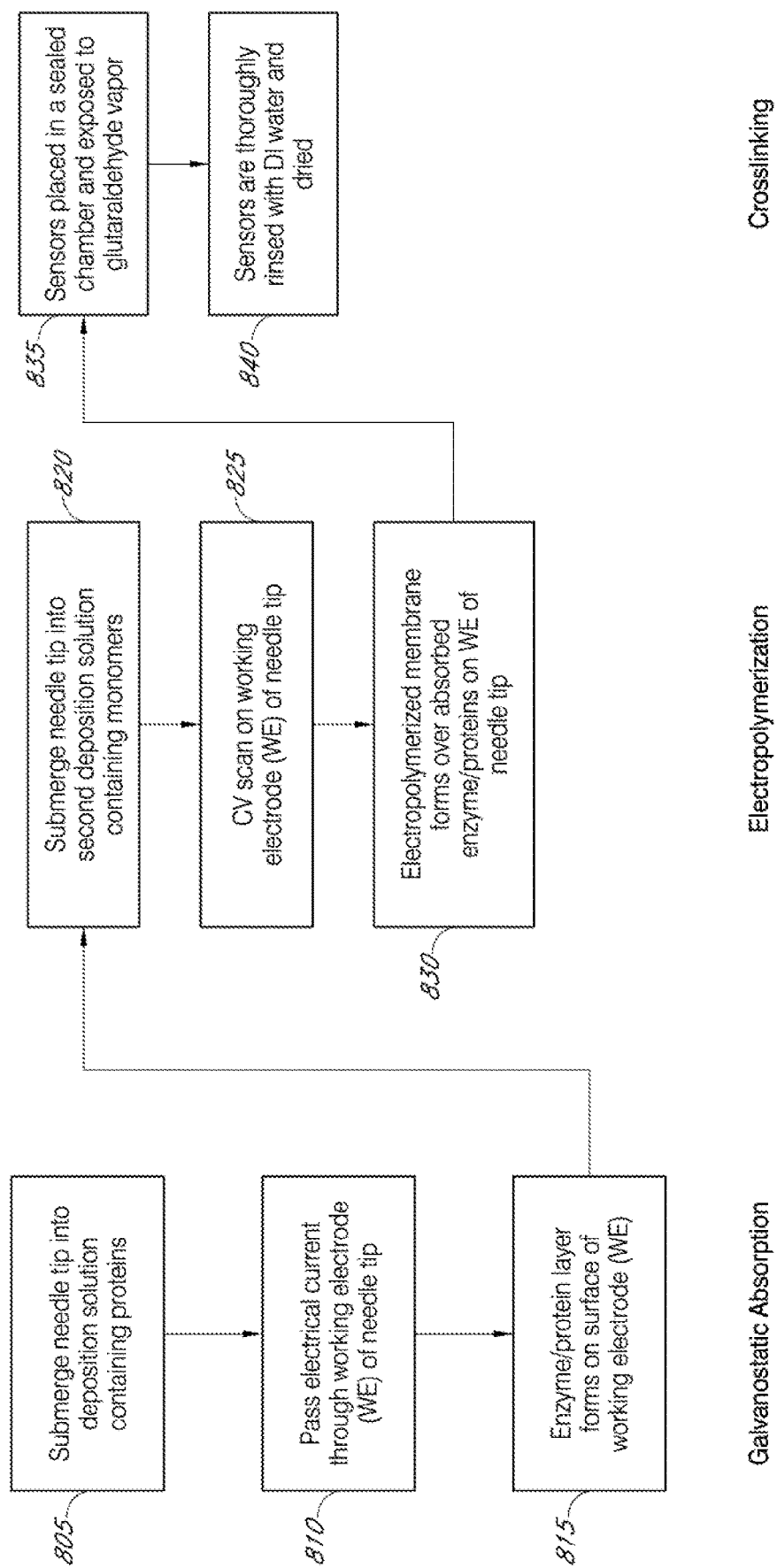
FIG. 8 is a flowchart showing a method for immobilizing an enzyme and diffusion limiting polymer on a working electrode of a biosensor needle tip, which includes stabilizing the enzyme matrix with vapor phase glutaraldehyde crosslinking in accordance with example embodiments of the invention

FIG. 8 is a flowchart showing a method for immobilizing an enzyme and diffusion limiting polymer on a working electrode of a biosensor needle tip, which includes stabilizing the enzyme matrix with glutaraldehyde crosslinking in accordance with example embodiments of the invention. The example here involves vapor phase crosslinking with glutaraldehyde. According to some example embodiments, the number and order of operations illustrated in FIG. 8 may vary. For example, according to some example embodiments, there may be fewer or additional operations, unless otherwise stated or implied to the contrary.

Referring to FIG. 8, GOx can be absorbed on the surface of an evaporated Pt working electrode (WE) using galvanostatic adsorption. In this embodiment, the needle sensor can be submerged into a GOx/HSA deposition solution in step 805. An external CE and/or an external RE can also be placed in the deposition solution. In some embodiments, the GOx/HSA deposition solution can be composed of 4% wt/vol GOx and 4% wt/vol HSA in PBS. While the needle sensor is submerged in the GOx/HSA deposition solution, an electrical current can be passed through the evaporated Pt WE in step 810, for example, by utilizing the external CE and/or the external RE. In some embodiments, the current can be set at 1 µA and be held between 50 and 60 seconds. The electric current polarizes the evaporated Pt WE, which attracts the GOx and HSA proteins in the deposition solution to the evaporated Pt WE surface. The electrostatic forces hold the GOx and HSA at the surface of the evaporated Pt substrate in step 815.

Subsequently, a polymer membrane can be formed over the GOx on the surface of the evaporated Pt WE using cyclic voltammetry (CV) electropolymerization or fixed potential (CV/FP) electropolymerization. This process may involve removing the needle sensor from the initial GOx/HSA deposition solution and submerging it into a different container having a second deposition solution which contains monomers in step 820. The external CE and/or the external RE can also be placed in the second deposition solution. In some embodiments, the second deposition solution can be composed of 5 mM tyramine in PBS. In step 825, CV can be used to reversibly scan the potential of the evaporated Pt WE, while the needle sensor is submerged in the second deposition solution, for example, by utilizing the external CE and/or the external RE. In some embodiments, the range of the CV scan can be 0 to 1.2V at a scan rate of 10 mV/sec for 1 cycle. The CV scan can result in a polytramine membrane deposited over the absorbed GOx on the evaporated Pt WE surface in step 830. The polytramine membrane may be glucose limiting.

After drying, the needle sensor can be elevated in a sealed crosslinking chamber in step 835 for the case of vapor phase glutaraldehyde crosslinking. The crosslinking step can be performed before or after the electropolymerization of the membrane and can depend on the type of polymer membrane being used. In some embodiments, the crosslinking chamber may contain a volume of 5% glutaraldehyde in DI water and may be performed after electrodeposition of polytyramine. After crosslinking, the needle sensors can be thoroughly rinsed in DI water in step 840.

Figure 9A:
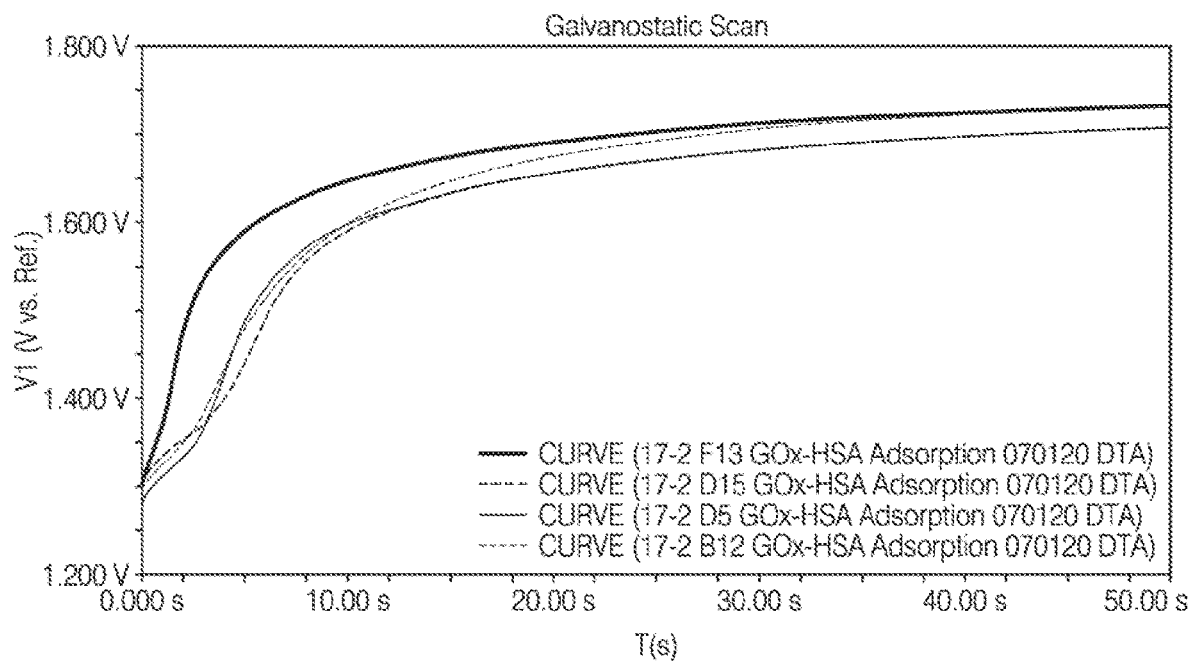
FIG. 9A shows the deposition trace for the galvanostatic absorption of enzyme onto the working electrode according to the method disclosed in FIG. 5.
Figure 9B:
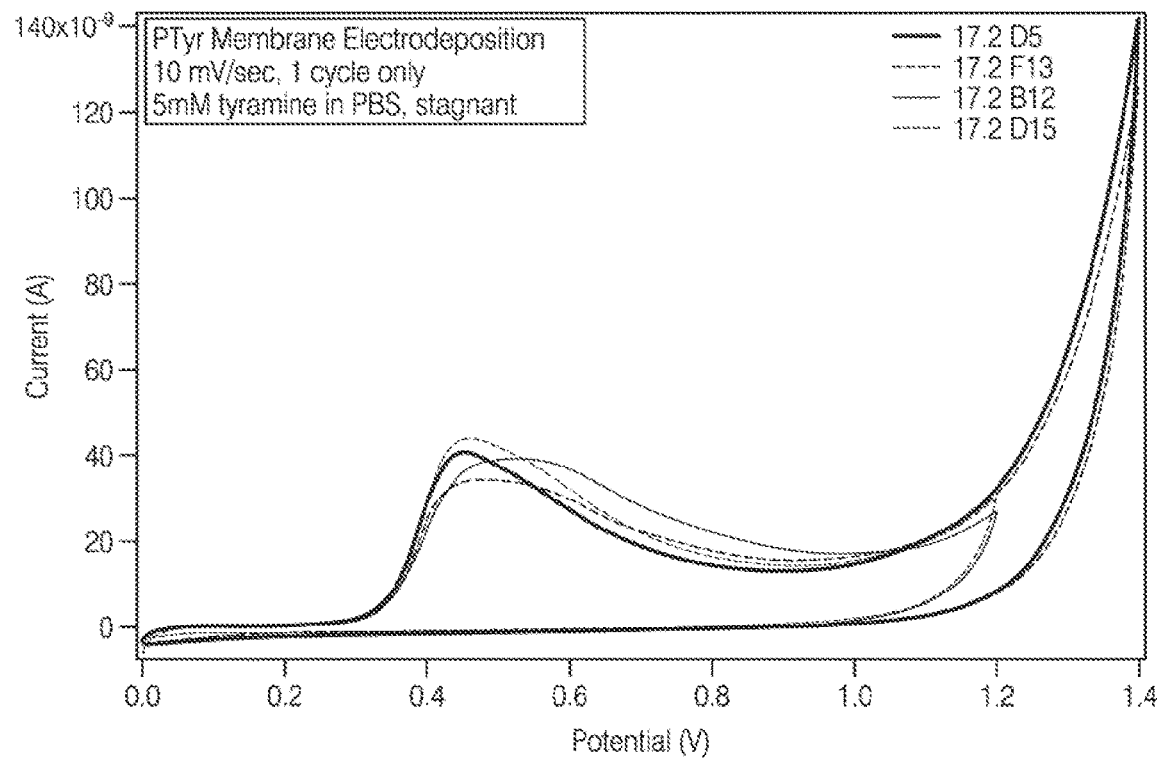
FIG. 9B shows the cyclic voltammetry trace for the deposition of the diffusion limiting membrane which encapsulates the enzyme according to the method disclosed in FIG. 5.
Figure 9C:
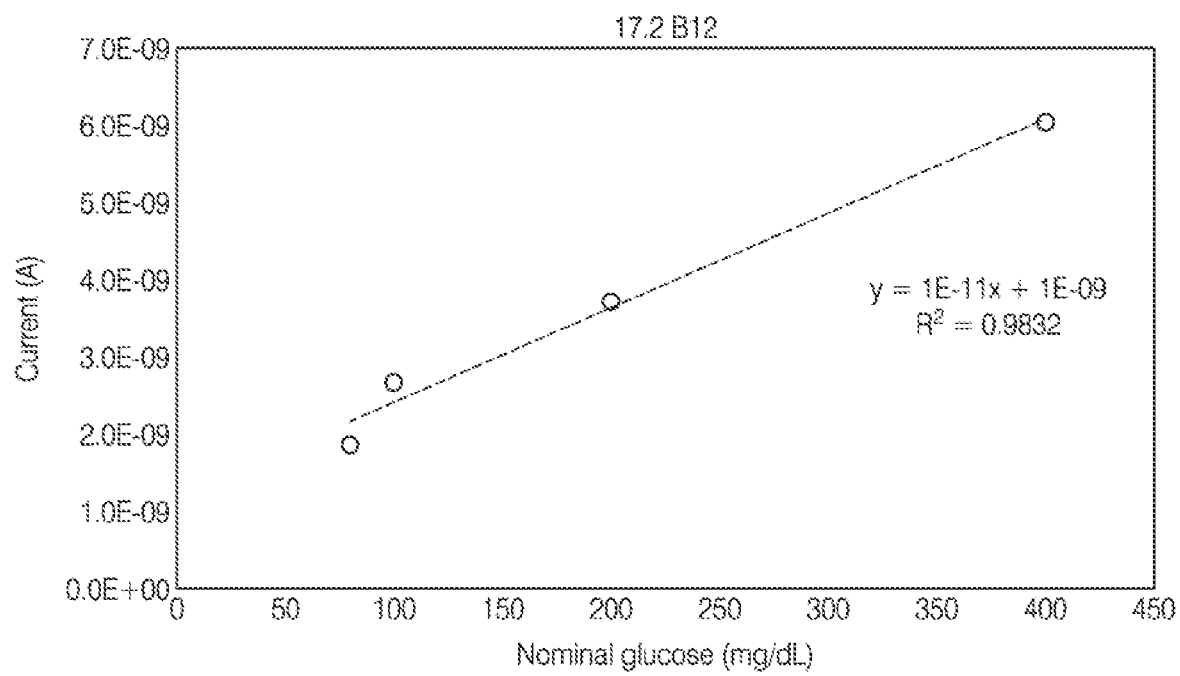
FIGS. 9C and 9D are examples of a linear response to glucose for sensors made according to the method disclosed in FIG. 8, where the devices are crosslinked.
Figure 9D:
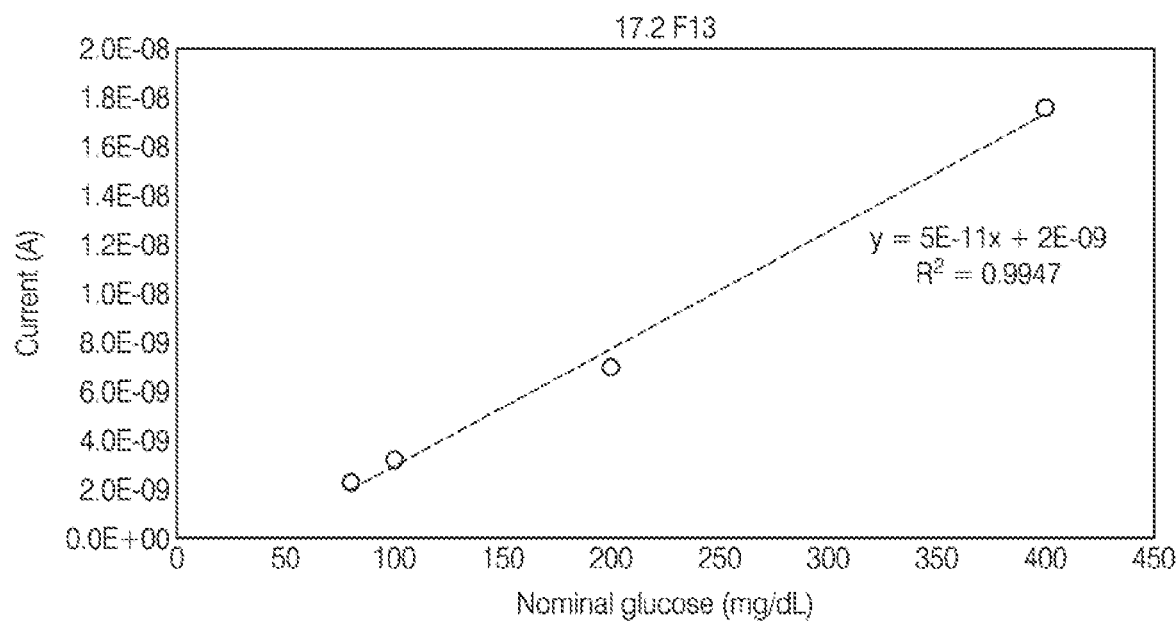

FIG. 9A shows the deposition trace for the galvanostatic absorption of enzyme onto the working electrode. FIG. 9B shows the cyclic voltammetry trace for the deposition of the diffusion limiting membrane which encapsulates the enzyme. Both the galvanostatic absorption of enzyme onto the working electrode in FIG. 9A and the deposition of the diffusion limiting membrane in FIG. 9B were performed according to the method disclosed in FIG. 5. FIGS. 9C and 9D are examples of a linear response to glucose for sensors made according to the method disclosed in FIG. 8, where the devices are crosslinked.

An alternative method for immobilizing an enzyme on an evaporated Pt biosensor electrode using a HSA deposition solution, in accordance with example embodiments of the disclosure, will now be described. According to some example embodiments, the number and order of operations described herein may also vary. For example, according to some example embodiments, there may be fewer or additional operations, unless otherwise stated or implied to the contrary.

In this alternative method, the needle sensor can be rinsed an additional time after the galvanostatic absorption and before the electropolymerization. Describing the entire alternative method in detail, the needle sensor can first be submerged into a GOx/HSA deposition solution with an external CE and/or an external RE. In some embodiments, the GOx/HSA deposition solution can be composed of 4% wt/vol GOx and 4% wt/vol HSA in PBS. An electrical current can then be passed through the evaporated Pt WE while the needle sensor is submerged in the GOx/HSA deposition solution, for example, by utilizing the external CE and/or the external RE. In some embodiments, the current can be set at 1 µA and be held between 50 and 60 seconds. The electric current polarizes the evaporated Pt WE, which attracts the GOx and HSA in the deposition solution to the evaporated Pt WE surface. The electrostatic forces hold the GOx and HSA at the surface of the evaporated Pt WE.

Subsequently, a polymer membrane can be formed over the GOx on the surface of the evaporated Pt WE using cyclic voltammetry (CV) electropolymerization. This process involves removing the evaporated needle sensor from the initial GOx/HSA deposition solution and submerging the needle sensor into a different container having a second deposition solution containing monomers. The external CE and/or the external RE can also be placed in the second deposition solution. In some embodiments, the second deposition solution can be composed of 5 mM tyramine in PBS. Using, for example, the external CE and/or the external RE, a CV can be used to change the potential of the evaporated Pt WE, while the needle sensor is submerged in the second deposition solution. In some embodiments, the range of the CV scan can be 0 to 1.2V at a scan rate of 10 mV/sec for 1 cycle. The CV scan can result in a polytramine membrane deposited over the absorbed GOx and HSA on the evaporated Pt WE surface. The polytramine membrane may be glucose limiting.

After drying, the needle sensor can be elevated in a sealed crosslinking chamber for the case of vapor phase glutaraldehyde crosslinking. The crosslinking step can be performed before or after the electropolymerization of the membrane and can depend on the type of polymer membrane being used. In some embodiments, the crosslinking chamber may contain a volume of 5% glutaraldehyde in DI water and may be performed after electrodeposition of polytyramine. After crosslinking, the needle sensors can be thoroughly rinsed in DI water.

Figure 10A:
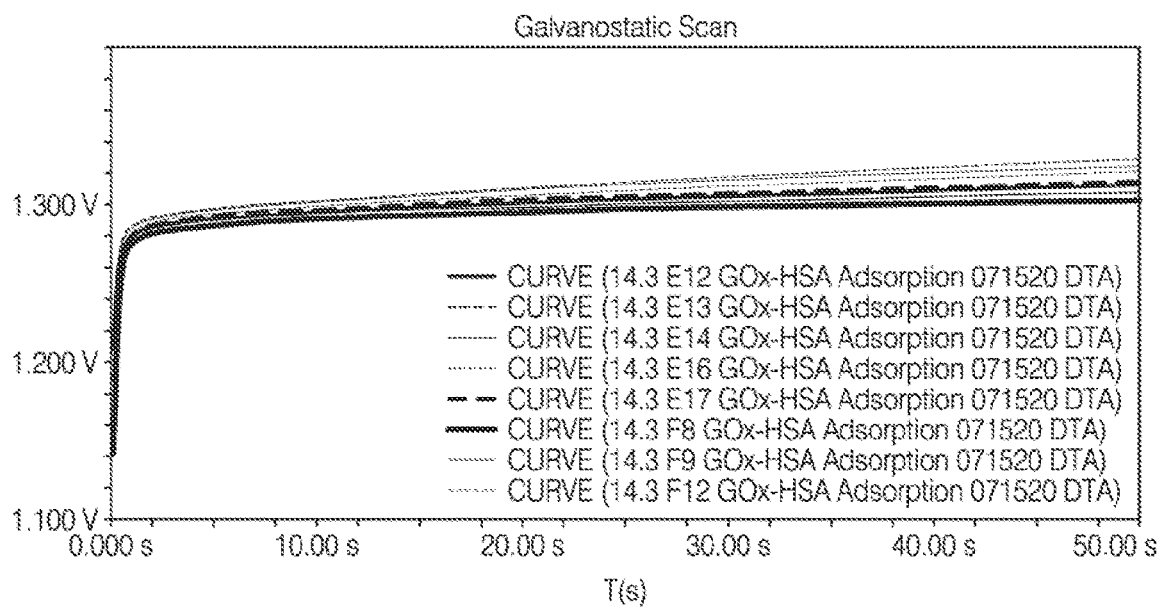
FIG. 10A shows the deposition trace for the galvanostatic absorption of enzyme onto the working electrode according to the method disclosed in FIG. 5.
Figure 10B:
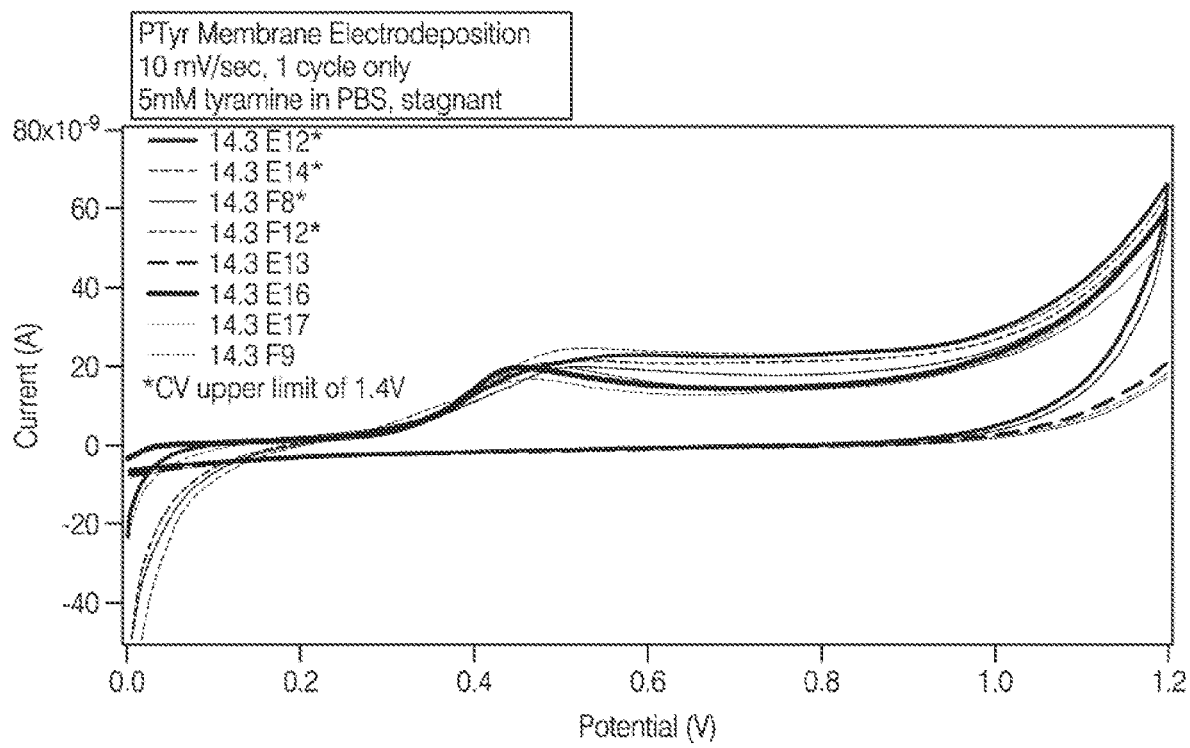
FIG. 10B shows the cyclic voltammetry trace for the deposition of the diffusion limiting membrane which encapsulates the enzyme according to the method disclosed in FIG. 5.
Figure 10C:
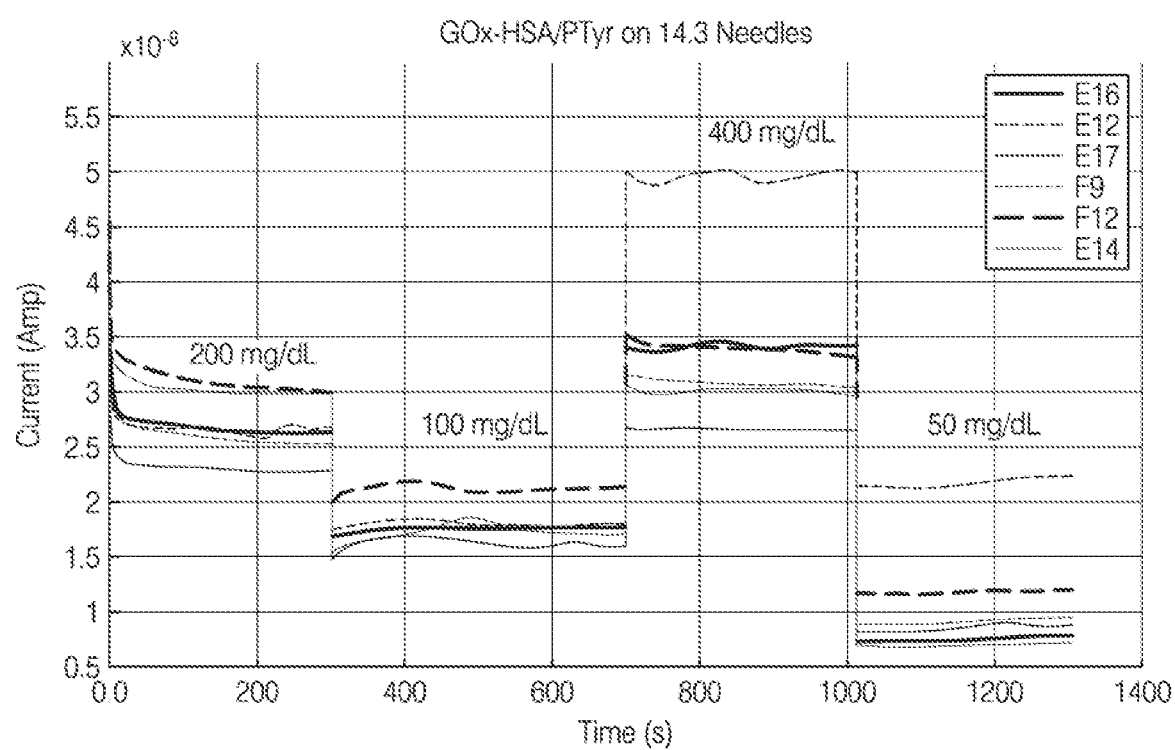
FIG. 10C shows the glucose response of a set of sensors that has been fabricated according to the method disclosed in FIG. 8.

FIG. 10A shows the deposition trace for the galvanostatic absorption of enzyme onto the working electrode according to the method disclosed in FIG. 5. FIG. 10B shows the cyclic voltammetry trace for the deposition of the diffusion limiting membrane which encapsulates the enzyme according to the method disclosed in FIG. 5. FIG. 10C shows the glucose response of a set of sensors that has been fabricated according to the method disclosed in FIG. 8.

The foregoing is illustrative of example embodiments, and is not to be construed as limiting thereof. Although a few example embodiments have been described, those skilled in the art will readily appreciate that many modifications are possible in the example embodiments without materially departing from the novel teachings and advantages of example embodiments. Accordingly, all such modifications are intended to be included within the scope of example embodiments as defined in the claims. Therefore, it is to be understood that the foregoing is illustrative of example embodiments and is not to be construed as limited to the specific embodiments disclosed, and that modifications to the disclosed example embodiments, as well as other example embodiments, are intended to be included within the scope of the appended claims. The inventive concept is defined by the following claims, with equivalents of the claims to be included therein.

What is claimed is:

1. A method for forming an enzymatic biosensor, the method comprising:
   preparing a first deposition solution comprising an enzyme;
   placing a substrate in the first deposition solution;
   applying an electrical potential to a working electrode of the substrate to deposit the enzyme on the working electrode;
   placing the substrate in a second deposition solution comprising electro-polymerizable monomers and 5 mM tyramine; and
   passing a current through the working electrode to polymerize the monomers to form an electropolymerized polymer layer over the enzyme deposited on the working electrode.

2. The method of claim 1, wherein the first deposition solution further comprises a stabilizing protein having a same effective charge as the enzyme.

3. The method of claim 2, wherein the stabilizing protein comprises human serum albumin (HSA).

4. The method of claim 2, wherein the stabilizing protein comprises silk fibroin.

5. The method of claim 1, further comprising crosslinking the enzyme deposited on the working electrode with solution phase or vapor phase crosslinking prior to depositing the electropolymerized polymer.

6. The method of claim 1, further comprising crosslinking the enzyme deposited on the working electrode with solution phase or vapor phase crosslinking after depositing the electropolymerized polymer.

7. The method of claim 1, wherein the enzyme comprises glucose oxidase (GOx).

8. The method of claim 1, wherein the working electrode comprises at least one of platinum, platinum black, carbon, iridium oxide, or platinum nanoparticles.

9. A method for immobilizing an enzyme on a biosensor electrode, the method comprising:
   submerging an electrode in a first deposition solution;
   passing an electrical current through the electrode to form an enzyme layer on the electrode;
   submerging the electrode in a second deposition solution comprising 5 mM tyramine;
   conducting a cyclic voltammetry (CV) scan of the electrode to form a polymer membrane over the enzyme layer on the electrode;
   rinsing the electrode with deionized water; and
   drying the electrode with a compressed gas.

10. The method of claim 9, further comprising elevating the electrode in a sealed crosslinking chamber to crosslink the enzyme.

11. The method of claim 9, wherein the first deposition solution comprises 4% wt/vol GOx in phosphate buffered saline (PBS), and filtered through a 0.2 µm polyethersulfone (PES) filter.

12. The method of claim 9, wherein the first deposition solution comprises 4% wt/vol GOx and 4% wt/vol HSA in PBS and filtered through a 0.8 µm PES filter.

13. The method of claim 9, wherein the electrical current is approximately 1 µA and is applied for approximately 50 to 60 seconds.

14. The method of claim 9, wherein the polymer membrane comprises a polytramine membrane.

15. The method of claim 9, wherein the CV scan is approximately 0 to 1.2 V with a scan rate of approximately 10 mV/sec for 1 cycle.

16. The method of claim 1, wherein the first deposition solution does not include a stabilizing protein.

17. A method for immobilizing an enzyme on a biosensor electrode, the method comprising:
- submerging an electrode in a first deposition solution that comprises 4% wt/vol GOx in PBS and that is filtered through a 0.2 µm PES filter;
- passing an electrical current through the electrode to form an enzyme layer on the electrode;
- submerging the electrode in a second deposition solution;
- conducting a CV scan of the electrode to form a polymer membrane over the enzyme layer on the electrode;
- rinsing the electrode with deionized water; and
- drying the electrode with a compressed gas.

18. The method of claim 17, wherein the first deposition solution further comprises a stabilizing protein.

19. The method of claim 18, wherein the stabilizing protein comprises HSA.

20. A method for immobilizing an enzyme on a biosensor electrode, the method comprising:
- submerging an electrode in a first deposition solution that comprises 4% wt/vol GOx and 4% wt/vol HSA in PBS and that is filtered through a 0.8 µm PES filter;
- passing an electrical current through the electrode to form an enzyme layer on the electrode;
- submerging the electrode in a second deposition solution;
- conducting a CV scan of the electrode to form a polymer membrane over the enzyme layer on the electrode;
- rinsing the electrode with deionized water; and
- drying the electrode with a compressed gas.

* * * * *